(12) United States Patent
Zaludek

(10) Patent No.: US 10,188,655 B2
(45) Date of Patent: Jan. 29, 2019

(54) LIQUID PHARMACEUTICAL COMPOSITION COMPRISING PEMETREXED

(71) Applicant: SYNTHON B.V., Nijmegen (NL)

(72) Inventor: Borek Zaludek, Blansko (CZ)

(73) Assignee: Synthon B.V., Nijmegen (NL)

( * ) Notice: Subject to any disclaimer, the term of this patent is extended or adjusted under 35 U.S.C. 154(b) by 0 days.

(21) Appl. No.: 15/990,035

(22) Filed: May 25, 2018

(65) Prior Publication Data

US 2018/0271872 A1    Sep. 27, 2018

Related U.S. Application Data

(63) Continuation of application No. 15/518,201, filed as application No. PCT/EP2015/073385 on Oct. 9, 2015.

(30) Foreign Application Priority Data

Oct. 16, 2014  (EP) .................................... 14189222

(51) Int. Cl.
| | | |
|---|---|---|
| A61K 31/519 | (2006.01) | |
| A61K 31/198 | (2006.01) | |
| A61K 47/18 | (2017.01) | |
| A61K 9/00 | (2006.01) | |
| A61K 47/10 | (2017.01) | |
| A61P 35/00 | (2006.01) | |

(52) U.S. Cl.
CPC .......... *A61K 31/519* (2013.01); *A61K 9/0019* (2013.01); *A61K 31/198* (2013.01); *A61K 47/10* (2013.01); *A61K 47/18* (2013.01); *A61K 47/183* (2013.01); *A61P 35/00* (2018.01)

(58) Field of Classification Search
None
See application file for complete search history.

(56) References Cited

U.S. PATENT DOCUMENTS 6,686,365 B2 *  2/2004  Riebesehl .............. A61K 45/06
                                                    514/262.1

FOREIGN PATENT DOCUMENTS

| CN | 101081301 A | * 12/2007 |
|---|---|---|
| EP | 432677 A1 | 6/1991 |
| EP | 2666463 A1 | 11/2013 |
| WO | WO 01/56575 A1 | 8/2001 |
| WO | WO 2012/015810 A2 | 2/2012 |
| WO | WO 2012/121523 | 9/2012 |
| WO | WO 2013/144814 | 10/2013 |
| WO | WO 2013/178214 | 12/2013 |
| WO | WO 2013/179248 A1 | 12/2013 |

OTHER PUBLICATIONS

FDA. Guidance for Industry: Sterile Drug Products. (2004).*

* cited by examiner

*Primary Examiner* — Deepak R Rao
*Assistant Examiner* — Laura M Daniel
(74) *Attorney, Agent, or Firm* — Buscher Patent PLLC

(57) ABSTRACT

The present invention relates to a liquid pharmaceutical composition suitable for parenteral administration comprising:
  a) pemetrexed diacid;
  b) at least one organic amine;
  c) at least one antioxidant;
  d) 10-200 mg/ml of propylene glycol; and
  e) one or more parenteral solvents,
wherein the preparation thereof is conducted in an atmosphere of inert gas and wherein the organic amine(s) is present in an amount sufficient to reach a pH of the composition in the range from 8.3 to 9.1
The invention further relates to the use of said liquid pharmaceutical composition as medicament in the treatment of malignant pleural mesothelioma and non-small cell lung cancer.

19 Claims, No Drawings

LIQUID PHARMACEUTICAL COMPOSITION COMPRISING PEMETREXED

CROSS REFERENCE TO RELATED APPLICATIONS

The present application is a continuation under 35 U.S.C. § 120 of copending U.S. application Ser. No. 15/518,201, filed Apr. 10, 2017, which is a U.S. national stage application under 35 U.S.C. § 371 of PCT International Application No. PCT/US2015/073385, which was filed on Oct. 9, 2015, which claims priority to European Application No. 14189222.4, which was filed on Oct. 16, 2014, the disclosure of which is incorporated by reference herein in its entirety.

BACKGROUND OF THE PRESENT INVENTION

Pemetrexed, chemically N-[4-[2-(2-amino-4,7-dihydro-4-oxo-1H-pyrrolo[2,3-d]pyrimidin-5-yl)ethyl]benzoyl]-L-glutamic acid of formula (I),

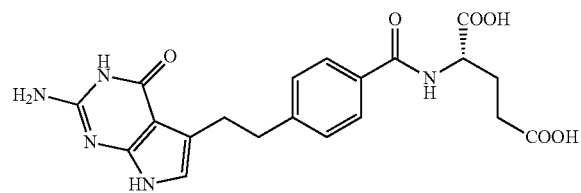

is a pharmaceutically active compound used for the treatment of malignant pleural mesothelioma and for second-line treatment of non-small cell lung cancer. The compound has been first disclosed in EP432677.

The disodium heptahydrate salt of pemetrexed is marketed by Eli Lilly under the brand name ALIMTA® and is supplied as a sterile lyophilized powder for intravenous infusion available in single-dose vials. The lyophilized product is available in the strengths of 100 mg and 500 mg per vial and is reconstituted with 0.9% saline solution at a concentration of 25 mg/ml. After further dilution with 0.9% saline solution to 100 ml it is then administered intravenously over 10 minutes.

It would be an advantage to have a stable, ready to use reconstituted solution that only has to be further diluted before administration. Particularly with potentially toxic pharmaceuticals like pemetrexed this would be desired, wherein such solution provides easier and safer handling for the caregiver. In addition, it would be particularly desirable if the stable formulation can be prepared without the use of freeze drying techniques.

It is known that a simple, isotonic saline solution of pemetrexed is not pharmaceutically acceptable for commercial purposes due to degradation into unacceptable related substances. The chemical instability of pemetrexed is mainly attributed to oxidative and acidic degradation. According to WO 2012015810, five major degradants of pemetrexed have been detected and identified. Under acidic conditions, decarboxylation of glutamic acid is observed. Under alkaline conditions, degradation proceeds by side chain amide hydrolysis followed by deamination. In the presence of oxygen, two oxidative degradants result.

In literature, several examples are given of stable solutions comprising pemetrexed. WO2012121523 discloses solutions for injection comprising pemetrexed, which are free of antioxidants. WO2013144814 discloses stable ready-to-use pharmaceutical compositions comprising pemetrexed, preferably the disodium salt, wherein the composition is free of antioxidants, amino acids and chelating agents. Both inventions claim that stability of the solutions is achieved by controlling the oxygen content of drug solution and vial headspace. Although in theory degradation could be prevented by controlling the oxygen content, in practice this is not easy to achieve.

WO0156575 discloses pharmaceutical compositions suitable for liquid parenteral administration comprising pemetrexed, preferably the disodium salt, at least one antioxidant, selected from monothioglycerol, L-cysteine and thioglycolic acid, and an excipient. WO2013179248 discloses liquid compositions, comprising pemetrexed, an organic amine, an inert gas and optionally one or more pharmaceutically acceptable excipients. WO2013178214 discloses liquid pharmaceutical solutions comprising pemetrexed, preferably the disodium salt, a solvent and an antioxidant, selected from acetylcysteine and sodium 2-mercaptoethanesulphonate. WO2012015810 discloses liquid compositions comprising pemetrexed, preferably the disodium salt, an antioxidant selected from lipoic acid, dihydrolipoic acid and methionine, a chelating agent selected from lactobionic acid and sodium citrate and a fluid.

Repetition of the examples cited in the prior art show that the long term stability of the disclosed compositions is insufficient. Moreover, some of the compositions are not desirable from a toxicological point of view.

Thus, in view of the prior art cited above, there is still a need for a ready to use reconstituted solution comprising pemetrexed, which is safe and exhibits excellent long term stability.

BRIEF DESCRIPTION OF THE PRESENT INVENTION

The present invention provides a liquid pharmaceutical composition suitable for parenteral administration comprising:
   a) pemetrexed diacid;
   b) at least one organic amine;
   c) at least one antioxidant;
   d) 10-200 mg/ml of propylene glycol; and
   e) one or more parenteral solvents, wherein the preparation thereof is conducted in an atmosphere of inert gas and wherein the organic amine(s) is present in an amount sufficient to reach a pH of the composition in the range from 8.3 to 9.1.

In addition, the liquid pharmaceutical composition of the present invention may optionally comprise at least one chelating agent.

It also provides a process for preparing said liquid pharmaceutical composition comprising dissolving the organic amine(s), pemetrexed diacid, the antioxidant(s), optionally the chelating agent(s) and propylene glycol in the solvent(s), making up the volume using water (for injection), filtrating and filling the glass vials.

Said liquid pharmaceutical composition may be used as medicament in the treatment of malignant pleural mesothelioma and non-small cell lung cancer.

DETAILED DESCRIPTION OF THE PRESENT INVENTION

As mentioned above, in literature, several examples are given of so-called stable solutions comprising pemetrexed.

However, we experienced that none of the disclosed compositions cited in the prior art exhibit sufficient long term stability and that in addition, some of the compositions are not desirable from a toxicological point of view. Experiments in our laboratory have led to the development of a ready to use reconstituted solution comprising pemetrexed, wherein a particular combination of components within a specific pH range results in a toxicological safe composition exhibiting excellent long term stability.

The present invention provides a liquid pharmaceutical composition suitable for parenteral administration comprising:
  a) pemetrexed diacid;
  b) at least one organic amine;
  c) at least one antioxidant;
  d) 10-200 mg/ml of propylene glycol, and
  e) one or more parenteral solvents,
wherein the preparation thereof is conducted in an atmosphere of inert gas and wherein the organic amine(s) is present in an amount sufficient to reach a pH of the composition in the range from 8.3 to 9.1.

The pharmaceutical composition of the present invention is free from pemetrexed disodium or sodium ions.

The solubility of pemetrexed diacid is very low in aqueous solutions with neutral or acidic pH. In order to obtain an aqueous solution wherein pemetrexed diacid is completely dissolved, one or more organic amines are added to the composition. Preferably, the organic amine is arginine. The arginine used in the present invention is preferably, but not limited to, the naturally occurring aminoacid L-arginine, which is cheap and readily available. The organic amine is present in at least 2.5 equivalents (mole/mole) with respect to pemetrexed diacid. In the first place, addition of the organic amine(s) serves the purpose of dissolving pemetrexed diacid. Furthermore, by using an excess of organic amine over pemetrexed diacid it also has the function of obtaining and maintaining the pH of the composition in the desired range.

In order to prevent acidic degradation of the composition of pemetrexed as much as possible, the pH of the liquid pharmaceutical composition of the present invention is in the range from 8.3 to 9.1. Preferably, the pH is between 8.5 and 8.8. The lower limit of the pH range suitable for the composition of the present invention is 8.3; below this value, precipitation was observed. The upper limit of the pH range for the composition of the present invention is 9.1. Above this pH value, the safety of administration of parenteral compositions into peripheral veins cannot be guaranteed.

The organic amine(s) is present in an amount sufficient to reach the desired pH range of the liquid pharmaceutical composition. In a preferred embodiment of the present invention, arginine is present in an amount sufficient to reach a pH of the liquid pharmaceutical composition in the range from 8.3 to 9.1.

Suitable antioxidants are those compounds which are pharmaceutically acceptable for use in human liquid pharmaceutical compositions. Common antioxidants, such as BHT (butylhydroxytoluene) and methionine do not provide the desired stability for the claimed composition. In fact, the compositions comprising these antioxidants gave rise to precipitation after 2 months of storage at 25° C. Surprisingly, the antioxidants most effective in the claimed composition are monothiolic antioxidants, viz. antioxidants containing one single thiol-functionality. Examples of such antioxidants are L-cysteine, monothioglycerol and thioglycolic acid. Most preferably, the antioxidant is L-cysteine.

The antioxidant is present in the composition of the present invention in concentrations of 0.5-10 mg/ml. When the antioxidant used is L-cysteine, the concentration is 0.5-4 mg/ml, preferably 1-2 mg/ml.

To further increase the stability of the liquid pharmaceutical composition of the present invention, 10-200 mg/ml of propylene glycol is added to the composition. In a preferred embodiment of the present invention, the water-soluble propylene glycol is present in concentrations of 20-50 mg/ml. These concentrations of propylene glycol are considered safe from a toxicological point of view, hereby also taking into account the relatively short administration time of the pemetrexed comprising liquid composition.

Without meaning to be bound by any theory or hypothesis, the propylene glycol, likely by increasing the viscosity of the composition, surprisingly prevents to a certain extent exposure of pemetrexed to oxygen and therefore contribute to enhancement of the stability of the composition towards oxidation.

The parenteral solvents used in the present invention are those solvents which are pharmaceutically acceptable for use in human liquid pharmaceutical compositions. The parenteral solvent of the present invention is selected from ethanol, isopropanol, dimethylsulfoxide, dimethylformamide, dimethylacetamide, glycerol and water or mixtures thereof. Preferably, the parenteral solvent is selected from ethanol, isopropanol, dimethylsulfoxide and water or a mixture thereof. Most preferably, the parenteral solvent is water or a mixture of alcohol and water. Water must be of pharmaceutically acceptable quality. Typically, water with the qualification "for injections", as defined in acknowledged Pharmacopoeias, is used.

For administration, water may comprise conventional tonicity agents assuring proper osmolarity, for instance sodium chloride, dextrose, mannitol, etc, in suitable non-limiting concentrations, e.g. an aqueous saline solution.

To further protect the composition of the present invention from oxidation, a chelating agent may be added optionally. It is common knowledge that metal ions induce oxidation. Without meaning to be bound by any theory or hypothesis, oxidation can be induced by metal ions leached from the surface of the glass vial or from the elastomeric composition of the stopper in which the pemetrexed composition is stored, or by metal ions already present in the solvents and/or additives used. The presence of a chelating agent stabilizes the pemetrexed solution during long-term storage. Suitable chelating agents include those which are pharmaceutically acceptable for use in human formulations. Preferably, the chelating agent used in the present invention is citric acid or tartaric acid. Most preferably, the chelating agent is citric acid. Due to the presence of arginine in the composition, arginine citrate will be formed in situ. Typically, the concentration of the chelating agent in the liquid composition is 1 mg/ml.

The present invention further provides a process for preparing the liquid pharmaceutical composition comprising dissolving the organic amine(s), pemetrexed diacid, the antioxidant(s), optionally the chelating agent(s) and propylene glycol in the solvent(s), making up the volume using water (for injection), filtrating and filling the glass vials. The process of the present invention is simple, reliable and cheap.

The liquid pharmaceutical composition of the present invention may optionally be sterilized using methods known to the artisan. Typically, the sterilization is carried out in an autoclave at 121° C. for 15 minutes. It is especially beneficial that the presently claimed liquid composition is stable during heat sterilization.

Advantageously, the liquid pharmaceutical composition is prepared by dissolving arginine in water for injection, followed by addition of successively pemetrexed diacid, L-cysteine, optionally citric acid, and propylene glycol. The total volume is made up with water for injection. The obtained solution is then filtered, filled into glass vials and sterilized.

The process for preparing the liquid composition of the present invention is conducted in an atmosphere of inert gas to minimize oxidation of pemetrexed. In addition, headspace oxygen and moisture from the sealable vessel have to be removed. This can be established by purging the sealable container with an inert gas. Such inert gasses are for example nitrogen, argon or helium, or mixtures thereof. The preferred gas is nitrogen.

The suitability of the composition of the present invention has been studied and confirmed in stability studies. For purposes of the present invention, the impurities present in the pemetrexed-comprising formulations during stability studies were detected by high performance liquid chromatography (HPLC) equipped with a UV detector operating at a suitable wavelength (typically 227 nm). The amount of impurities was calculated on a normalized peak area response ("PAR") basis. As an acceptable limit demonstrating sufficient stability at the corresponding sampling point, the sum of peaks of all individual impurities in the invention compositions should not exceed 2% of the total PAR. The peak size of any individual impurity should not exceed 1% of the total PAR.

A sum of peaks of all individual impurities of below 3% of the total PAR after 6 months at 25° C. indicates sufficient stability for at least 18 months at 2-8° C.

Thus, the preferred compositions of the present invention are characterized in that they exhibit, after 6 months of storage in a closed container at 25° C., less than 3% of total impurities. Alternatively, the preferred compositions of the present invention are characterized in that they exhibit, after 18 months of storage in a closed container at 2-8° C., less than 2 percent of total impurities.

Accordingly, the temperatures at which the compositions of the present invention are kept for routine storage, within the period of the pharmaceutical shelf-life of the composition, are preferably between 2 and 8° C. The compositions are preferably stored in tightly stoppered original containers, typically closed glass vials. Under such conditions, the expected shelf-life of the compositions of the present invention is at least 18 months. It should be understood that the pemetrexed-comprising solutions remain in the temperature range described herein for substantially the entire period of storage before dilution and/or administration to the patient in need thereof.

The liquid pharmaceutical composition in accordance with the present invention may be used as a medicament. The pharmaceutical composition typically may be used in the treatment of malignant pleural mesothelioma and non-small cell lung cancer.

The following examples are intended to illustrate the scope of the present invention but not to limit it thereto.

EXAMPLES

General Procedure for the Preparation of the Liquid Pharmaceutical Composition

The liquid pharmaceutical compositions of examples 1-23, as described below, were prepared by using the following procedure.

Nitrogen was bubbled through water for injection for about 20 minutes. The organic amine was added to the appropriate amount of water under stirring. Pemetrexed diacid was added to the solution and the resulting mixture was stirred until complete dissolution was obtained. The antioxidant was added. In case of BHT (butylhydroxytoluene), a solution of BHT in ethanol was added. Optionally, the chelating agent was added. Propylene glycol was added and the mixture was stirred for 10 minutes. The volume of the obtained solution was made up to 1 ml with water for injection. The whole process of dissolving was carried out under a protective atmosphere of nitrogen (except for the procedure of example 4). The solution was filtered over a 0.22 microns Durapore membrane filter, filled into glass vials under nitrogen atmosphere and the vials were closed. Optionally, the prepared injection solutions were sterilized in an autoclave at 121° C. for 15 minutes.

Stability Study

The compositions were tested in a stability study at 25 and 40° C. in closed glass vials. Impurities were detected by high performance liquid chromatography (HPLC) equipped with a UV detector operating at 227 nm. The amount of impurities was calculated on a normalized peak area response ("PAR") basis.

Results

Cysteine Concentration

|  | Composition | | | |
| --- | --- | --- | --- | --- |
|  | PXD mg/ml | Arginine mg/ml | Propylene Glycol mg/ml | Cysteine mg/ml |
| Example 1 | 50 | 60 | 200 | 1 |
| Example 2 | 50 | 60 | 200 | 2 |

Samples were prepared in an atmosphere of nitrogen

Example 1: Stability Results

A) Without Steam Sterilization

| Name | Zero | 1 m/25° C. | 3 m/25° C. | 6 m/25° C. |
| --- | --- | --- | --- | --- |
| Appearance | Pale yellow solution | Pale yellow solution | Pale yellow solution | Yellow solution |
| pH | 8.99 | 8.90 | 8.92 | 8.85 |
| Color | GY4-GY5 | <Y3-<GY3 | <Y4 | GY2-GY3 |
| Clarity | <I | <I | <I | <I |
| PXD (mg/ml) | 53.05 | 50.04 | 50.52 | 49.64 |
| ΣIMP (% IN) | 0.34 | 0.58 | 0.37 | 0.41 |

B) Sterilized by Steam 121° C./15 Min

| Name | Zero | 1 m/25° C. | 6 m/25° C. |
| --- | --- | --- | --- |
| Appearance | Pale yellow solution | Pale yellow solution | Dark yellow solution |
| pH | 8.97 | 8.92 | 8.86 |
| Color | GY4-GY5 | <Y6 | out of scale |
| Clarity | <I | <I | <I |
| PXD (mg/ml) | 53.74 | 49.97 | 50.26 |
| ΣIMP (% IN) | 0.52 | 0.40 | 0.94 |

Example 2: Stability Results

A) Without Steam Sterilization

| Name | Zero | 1 m/25° C. | 3 m/25° C. | 6 m/25° C. |
|---|---|---|---|---|
| Appearance | Pale yellow solution | Pale yellow solution | Pale yellow solution | Pale yellow solution |
| pH | 8.98 | 8.91 | 8.88 | 8.86 |
| Color | GY4-GY5 | <Y7 | <Y6 | <Y6 |
| Clarity | <I | <I | <I | <I |
| PXD (mg/ml) | 52.82 | 50.59 | 51.91 | 50.51 |
| ΣIMP (% IN) | 0.34 | 0.37 | 0.30 | 0.26 |

B) Sterilized by Steam 121° C./15 Min

| Name | Zero | 1 m/25° C. | 6 m/25° C. |
|---|---|---|---|
| Appearance | Pale yellow solution | Pale yellow solution | Colorless solution |
| pH | 8.96 | 8.90 | 8.84 |
| Color | GY4-GY5 | <Y7 | <Y7 |
| Clarity | <I | <I | <I |
| PXD (mg/ml) | 54.32 | 50.63 | 51.13 |
| ΣIMP (% IN) | 0.47 | 0.38 | 0.27 |

Inert Atmosphere of Nitrogen

| | Composition | | | | | |
|---|---|---|---|---|---|---|
| | PXD mg/ml | Arginine mg/ml | Propylene Glycol mg/ml | Cysteine mg/ml | Tartaric Acid mg/ml | NITROGEN |
| Example 3 | 25 | 30 | 100 | 1 | 1 | YES |
| Example 4 | 25 | 30 | 100 | 1 | 1 | NO |

Example 3: Stability Results

Without Steam Sterilization

| Name | Zero | 1 m/40° C. | 2 m/40° C. |
|---|---|---|---|
| Appearance | Colorless solution | Colorless solution | Colorless solution |
| pH | 8.99 | 8.93 | not measured |
| Color | <B9 | <B9 | <B9 |
| Clarity | <I | <I | <I |
| PXD (mg/ml) | 25.85 | 25.87 | 25.09 |
| ΣIMP (% IN) | 0.18 | 0.30 | 0.26 |

Example 4: Stability Results

Without Steam Sterilization

| Name | Zero | 1 m/40° C. | 2 m/40° C. |
|---|---|---|---|
| Appearance | Colorless solution | Yellow solution | Dark yellow solution |
| pH | 8.99 | 8.89 | not measured |
| Color | <B9 | Y3 | out of scale |
| Clarity | <I | <I | <I |
| PXD (mg/ml) | 25.36 | 25.02 | 23.70 |
| ΣIMP (% IN) | 0.16 | 2.72 | 4.19 | pH/Varying Amounts of Arginine

| | Composition | | | | | |
|---|---|---|---|---|---|---|
| | PXD mg/ml | Arginine mg/ml | Propylene Glycol mg/ml | Cysteine mg/ml | Citric Acid mg/ml | pH* |
| Example 5 | 25 | 30 | 100 | 2 | 1 | 8.5 |
| Example 6 | 25 | 40 | 100 | 2 | 1 | 8.9 |
| Example 7 | 25 | 40 | 100 | 2 | 1 | 9.4 |

*At pH values below 8.3, precipitation occurred

Samples were prepared in an atmosphere of nitrogen

Value of pH = 9.4 was adjusted by addition of extra amount of L-arginine

Example 5: Stability Results

Sterilized by Steam 121° C./15 Min

| Name | Zero | 1 m/25° C. | 2 m/25° C. | 3 m/25° C. |
|---|---|---|---|---|
| Appearance | Colorless solution | Colorless solution | Colorless solution | Colorless solution |
| pH | 8.46 | 8.52 | 8.52 | 8.55 |
| Color | <BY9 | <BY9 | <BY9 | <BY9 |
| Clarity | <I | <I | <I | <I |
| PXD (mg/ml) | 25.39 | 25.86 | 25.69 | 25.76 |
| ΣIMP (% IN) | 0.21 | 0.20 | 0.24 | 0.26 |

Example 6: Stability Results

Sterilized by Steam 121° C./15 Min

| Name | Zero | 1 m/25° C. | 2 m/25° C. | 3 m/25° C. |
|---|---|---|---|---|
| Appearance | Colorless solution | Colorless solution | Colorless solution | Colorless solution |
| pH | 8.89 | 8.92 | 8.88 | 8.91 |
| Color | <BY9 | <BY9 | <BY9 | <BY9 |
| Clarity | <I | <I | <I | <I |
| PXD (mg/ml) | 24.94 | 25.25 | 25.83 | 25.84 |
| ΣIMP (% IN) | 0.16 | 0.23 | 0.20 | 0.18 |

Example 7: Stability Results

Sterilized by Steam 121° C./15 Min

| Name | Zero | 1 m/25° C. | 2 m/25° C. | 3 m/25° C. |
|---|---|---|---|---|
| Appearance | Colorless solution | Colorless solution | N/A | Colorless solution |
| pH | 9.39 | 9.41 | N/A | 9.42 |
| Color | <BY9 | <BY9 | N/A | <BY9 |
| Clarity | <I | <I | N/A | <I |
| PXD (mg/ml) | 24.32 | 25.69 | N/A | 24.91 |
| ΣIMP (% IN) | 0.23 | 0.26 | N/A | 0.28 |

Propylene Glycol Concentration

|  | Composition | | | |
| --- | --- | --- | --- | --- |
|  | PXD mg/ml | Arginine mg/ml | Propylene Glycol mg/ml | Cysteine mg/ml |
| Example 8 | 25 | 30 | — | 1 |
| Example 9 | 25 | 30 | 50 | 1 |
| Example 10 | 25 | 30 | 100 | 1 |

Samples were prepared in an atmosphere of nitrogen

Example 8: Stability Results

Without Steam Sterilization

| Name | Zero | 1 m/40° C. | 2 m/40° C. |
| --- | --- | --- | --- |
| Appearance | Almost colorless solution | Pale yellow solution | Pale yellow solution |
| pH | 8.85 | 8.95 | 8.95 |
| Color | <BY7 | <Y4 | Y3-Y4 |
| Clarity | <I | <I | <I |
| PXD (mg/ml) | 25.01 | 24.25 | 24.64 |
| ΣIMP (% IN) | 0.22 | 1.66 | 2.75 |

Example 9: Stability Results

Without Steam Sterilization

| Name | Zero | 1 m/40° C. | 2 m/40° C. |
| --- | --- | --- | --- |
| Appearance | Almost colorless solution | N/A | Yellowish solution |
| pH | 8.86 | N/A | 8.87 |
| Color | <BY7 | N/A | GY2-GY3 |
| Clarity | <I | N/A | <I |
| PXD (mg/ml) | 25.31 | N/A | 24.74 |
| ΣIMP (% IN) | 0.19 | N/A | 1.91 |

Example 10: Stability Results

Without Steam Sterilization

| Name | Zero | 1 m/40° C. | 2 m/40° C. |
| --- | --- | --- | --- |
| Appearance | Almost colorless solution | Pale green-yellow solution | Pale yellow solution |
| pH | 8.85 | 8.91 | 8.93 |
| Color | <BY7 | <Y5 | GY2-GY3 |
| Clarity | <I | <I | <I |
| PXD (mg/ml) | 25.18 | 25.23 | 24.98 |
| ΣIMP (% IN) | 0.18 | 0.55 | 1.13 |

Chelating Agent

|  | Composition | | | | | |
| --- | --- | --- | --- | --- | --- | --- |
|  | PXD mg/ml | Arginine mg/ml | Propylene Glycol mg/ml | Cysteine mg/ml | Tartaric acid mg/ml | Citric acid mg/ml |
| Example 11 | 25 | 30 | 100 | 1 | — | — |
| Example 12 | 25 | 30 | 100 | 1 | 1 | — |
| Example 13 | 25 | 30 | 100 | 1 | — | 1 |

Samples were prepared in an atmosphere of nitrogen

Example 11: Stability Results

Without Steam Sterilization

| Name | Zero | 1 m/40° C. | 2 m/40° C. |
| --- | --- | --- | --- |
| Appearance | Colorless solution | Pale yellow green solution | Pale yellow solution |
| pH | 8.85 | 8.91 | 8.93 |
| Color | <BY7 | <Y5 | GY2-GY3 |
| Clarity | <I | <I | <I |
| PXD (mg/ml) | 25.18 | 25.23 | 24.98 |
| ΣIMP (% IN) | 0.18 | 0.55 | 1.13 |

Example 12: Stability Results

Without Steam Sterilization

| Name | Zero | 1 m/40° C. | 2 m/40° C. |
| --- | --- | --- | --- |
| Appearance | Colorless solution | Colorless solution | Colorless solution |
| pH | 8.99 | 8.93 | N/A |
| Color | <B9 | <B9 | <B9 |
| Clarity | <I | <I | <I |
| PXD (mg/ml) | 25.85 | 25.87 | 25.09 |
| ΣIMP (% IN) | 0.18 | 0.30 | 0.26 |

Example 13: Stability Results

Without Steam Sterilization

| Name | Zero | 1 m/40° C. | 2 m/40° C. |
| --- | --- | --- | --- |
| Appearance | Colorless solution | Pale yellow solution | Pale yellow solution |
| pH | 8.99 | 9.03 | 9.09 |
| Color | <B9 | Y4 | Y4 |
| Clarity | <I | <I | <I |
| PXD (mg/ml) | 25.93 | 25.14 | 25.49 |
| ΣIMP (% IN) | 0.17 | 0.77 | 0.56 |

Antioxidant

| | Composition | | | | | |
|---|---|---|---|---|---|---|
| | PXD mg/ml | Arginine mg/ml | Propylene Glycol mg/ml | Cysteine mg/ml | N-acetyl-L-cysteine mg/ml | Methionine mg/ml | BHT mg/ml |
| Ex. 14 | 50 | 50 | 200 | | | | 0.15 |
| Ex. 15 | 50 | 60 | 200 | | | 1 | |
| Ex. 16 | 50 | 60 | 200 | | | 2 | |
| Ex. 17 | 50 | 60 | 200 | 1 | | | |
| Ex. 18 | 50 | 60 | 200 | 2 | | | |
| Ex. 19 | 25 | 30 | 100 | | 5 | | |

Samples were prepared in an atmosphere of nitrogen

Example 14: Stability Results

Without Steam Sterilization

| Name | Zero | 1 m/25° C. | 2 m/25° C. |
|---|---|---|---|
| Appearance | Pale yellow solution | Pale yellow solution | Stability testing terminated due to precipitation |
| pH | 8.56 | 8.53 | |
| Color | BY6 | <Y3 | |
| Clarity | <I | <I | |
| PXD (mg/ml) | 51.88 | 53.36 | |
| ΣIMP (% IN) | 0.25 | 1.01 | |

Example 15: Stability Results

Without Steam Sterilization

| Name | Zero | 1 m/25° C. | 2 m/25° C. |
|---|---|---|---|
| Appearance | Pale yellow solution | Pale yellow solution | Stability testing terminated due to precipitation |
| pH | 8.93 | 8.84 | |
| Color | BY6 | Y4 | |
| Clarity | <I | <I | |
| PXD (mg/ml) | 49.74 | 49.55 | |
| ΣIMP (% IN) | 0.33 | 1.26 | |

Example 16: Stability Results

Without Steam Sterilization

| Name | Zero | 1 m/25° C. | 2 m/25° C. |
|---|---|---|---|
| Appearance | Pale yellow solution | Pale yellow solution | Stability testing terminated due to precipitation |
| pH | 8.92 | 8.93 | |
| Color | BY5 | Y4 | |
| Clarity | <I | <I | |
| PXD (mg/ml) | 49.14 | 49.27 | |
| ΣIMP (% IN) | 0.41 | 1.35 | |

Example 17: Stability Results

Without Steam Sterilization

| Name | Zero | 1 m/25° C. | 3 m/25° C. |
|---|---|---|---|
| Appearance | Pale yellow solution | Pale yellow solution | Pale yellow solution |
| pH | 8.99 | 8.90 | 8.92 |
| Color | GY4-GY5 | <Y3-GY3 | <Y4 |
| Clarity | <I | <I | <I |
| PXD (mg/ml) | 53.05 | 50.04 | 50.52 |
| ΣIMP (% IN) | 0.34 | 0.58 | 0.37 |

Example 18: Stability Results

Without Steam Sterilization

| Name | Zero | 1 m/25° C. | 3 m/25° C. |
|---|---|---|---|
| Appearance | Pale yellow solution | Pale yellow solution | Pale yellow solution |
| pH | 8.98 | 8.91 | 8.88 |
| Color | GY4-GY5 | <Y7 | <Y6 |
| Clarity | <I | <I | <I |
| PXD (mg/ml) | 52.82 | 50.59 | 51.91 |
| ΣIMP (% IN) | 0.38 | 0.37 | 0.30 |

Example 19: Stability Results

Without Steam Sterilization

| Name | Zero | 1 m/25° C. | 3 m/25° C. |
|---|---|---|---|
| Appearance | Almost colorless solution | Almost colorless solution | N/A |
| pH | 8.39 | 8.43 | N/A |
| Color | <BY7 | <BY7 | N/A |
| Clarity | <I | <I | N/A |
| PXD (mg/ml) | 25.70 | 25.33 | N/A |
| ΣIMP (% IN) | 0.22 | 1.43 | N/A |

Influence of Steam Sterilization

| | Composition | | | | | |
|---|---|---|---|---|---|---|
| | PXD mg/ml | Arginine mg/ml | Propylene Glycol mg/ml | Cysteine mg/ml | Citric acid mg/ml | Steam sterilization |
| Example 20 | 25 | 40 | 50 | 2 | 1 | Without |
| Example 21 | 25 | 40 | 50 | 2 | 1 | 121° C./15 min |
| Example 22 | 25 | 30* | 50 | 2 | — | Without |
| Example 23 | 25 | 30* | 50 | 2 | — | 121° C./15 min |

Samples were prepared in an atmosphere of nitrogen

Example 20: Stability Results

| Name | Zero | 1 m/25° C. | 2 m/25° C. | 3 m/25° C. |
|---|---|---|---|---|
| Appearance | Colorless solution | Colorless solution | Colorless solution | Colorless solution |
| pH | 8.99 | 9.04 | 9.01 | 8.97 |
| Color | <BY9 | <BY9 | <BY9 | <BY9 |
| Clarity | <I | <I | <I | <I |
| PXD (mg/ml) | 24.93 | 24.67 | 24.97 | 24.62 |
| ΣIMP (% IN) | 0.21 | 0.22 | 0.24 | 0.22 |

Example 21: Stability Results

| Name | Zero | 1 m/25° C. | 2 m/25° C. | 3 m/25° C. |
|---|---|---|---|---|
| Appearance | Colorless solution | Colorless solution | Colorless solution | Colorless solution |
| pH | 8.98 | 9.01 | 9.00 | 8.96 |
| Color | <BY9 | <BY9 | <BY9 | <BY9 |
| Clarity | <I | <I | <I | <I |
| PXD (mg/ml) | 24.81 | 24.59 | 24.75 | 24.96 |
| ΣIMP (% IN) | 0.20 | 0.24 | 0.25 | 0.29 |

Example 22: Stability Results

| Name | Zero | 1 m/25° C. | 2 m/25° C. | 3 m/25° C. |
|---|---|---|---|---|
| Appearance | Colorless solution | Colorless solution | Colorless solution | Colorless solution |
| pH | 8.94 | 8.91 | 8.95 | 8.97 |
| Color | <BY9 | <BY9 | <BY9 | <BY9 |
| Clarity | <I | <I | <I | <I |
| PXD (mg/ml) | 24.80 | 24.34 | 25.05 | 25.02 |
| ΣIMP (% IN) | 0.24 | 0.25 | 0.24 | 0.29 |

Example 23: Stability Results

| Name | Zero | 1 m/25° C. | 2 m/25° C. | 3 m/25° C. |
|---|---|---|---|---|
| Appearance | Colorless solution | Colorless solution | Colorless solution | Colorless solution |
| pH | 8.92 | 8.89 | 8.95 | 8.94 |
| Color | <BY9 | <BY9 | <BY9 | <BY9 |
| Clarity | <I | <I | <I | <I |
| PXD (mg/ml) | 24.73 | 25.01 | 24.94 | 24.99 |
| ΣIMP (% IN) | 0.29 | 0.28 | 0.29 | 0.30 |

The invention claimed is:

1. A liquid pharmaceutical composition suitable for parenteral administration comprising:
   a. 25-50 mg/ml of pemetrexed diacid;
   b. arginine;
   c. at least one monothiolic antioxidant;
   d. 10-200 mg/ml of propylene glycol, and
   e. one or more parenteral solvents,
   wherein the preparation thereof is conducted in an atmosphere of inert gas and wherein the amount of arginine as a molar ratio to pemetrexed diacid is at least 2.5:1 (arginine:pemetrexed diacid) and said amount of arginine is sufficient to reach a pH of the composition in the range from 8.3 to 9.1.

2. The composition according to claim 1, wherein the monothiolic antioxidant is L-cysteine.

3. The composition according to claim 2, wherein L-cysteine is present in a concentration of 0.5-4 mg/ml.

4. The composition according to claim 1, wherein the concentration of propylene glycol is in the range of 20-50 mg/ml.

5. The composition according to claim 1, wherein the parenteral solvent is selected from: ethanol, isopropanol, dimethyl sulfoxide, dimethylformamide, dimethylacetamide, glycerol, water, and mixtures thereof.

6. The composition according to claim 1, wherein the parenteral solvent is water.

7. The composition according to claim 1, further comprising at least one chelating agent.

8. The composition according to claim 7, wherein the chelating agent is citric acid.

9. A process for preparing a liquid pemetrexed pharmaceutical composition, which comprises:
   dissolving arginine, pemetrexed diacid, monothiolic antioxidant(s), and propylene glycol in a parenteral solvent to form a liquid composition; and
   optionally adding water to said liquid composition;
   wherein said liquid composition has a pH in the range of 8.3 to 9.1; said arginine and pemetrexed diacid were dissolved in a molar ratio of at least 2.5:1 (arginine:

pemetrexed diacid); and said propylene glycol is present in said liquid composition in a concentration of 10 to 200 mg/ml.

10. The process according to claim 9 comprising the step of terminal sterilization.

11. The process according to claim 9, which further comprises filtrating said composition and filling it into glass vials.

12. The process according to claim 9, which further comprises:
    bubbling inert gas through said solvent before the dissolving step; and
    carrying out the dissolving step under an atmosphere of inert gas.

13. The process according to claim 12, wherein said dissolving step comprises first dissolving said arginine in said solvent and subsequently dissolving said pemetrexed diacid into said solvent.

14. A liquid pemetrexed pharmaceutical composition made by the process of claim 12.

15. The liquid pemetrexed pharmaceutical composition according to claim 14, wherein said monothiolic antioxidant is L-cysteine and said L-cysteine is present in said composition in a concentration of 0.5-4 mg/ml.

16. The liquid pemetrexed pharmaceutical composition according to claim 15, which further comprises citric acid.

17. The liquid pemetrexed pharmaceutical composition according to claim 15, wherein said pemetrexed is present in said composition in a concentration of 25-50 mg/ml.

18. The liquid pemetrexed pharmaceutical composition according to claim 15, wherein said parenteral solvent is water or a mixture of alcohol and water.

19. The composition according to claim 1, wherein said composition is free from pemetrexed disodium.

* * * * *